United States Patent [19]

Bennett

[11] Patent Number: 5,439,475
[45] Date of Patent: Aug. 8, 1995

[54] TISSUE GRAFTING METHOD USING AN APPARATUS WITH MULTIPLE TISSUE RECEIVING RECEPTACLES

[76] Inventor: David M. Bennett, Suite 12, 127 Nerang, St. Southport, Queensland, Australia

[21] Appl. No.: 961,730
[22] PCT Filed: Jul. 3, 1991
[86] PCT No.: PCT/AU91/00286
 § 371 Date: Jan. 7, 1993
 § 102(e) Date: Jan. 7, 1993
[87] PCT Pub. No.: WO92/00706
 PCT Pub. Date: Jan. 23, 1992

[30] Foreign Application Priority Data
Jul. 3, 1990 [AU] Australia .................. PK0958

[51] Int. Cl.⁶ .............................................. A61B 17/00
[52] U.S. Cl. ........................................ 606/187; 604/62
[58] Field of Search ............... 623/15; 604/48, 49, 604/51, 57, 59–64; 606/1, 131, 133, 187, 184–186; 128/898

[56] References Cited

U.S. PATENT DOCUMENTS

| | | | |
|---|---|---|---|
| 3,867,942 | 2/1975 | Bellantoni et al. | 606/131 |
| 4,451,254 | 5/1984 | Dinius et al. | 604/62 |
| 4,787,384 | 11/1988 | Campbell et al. | 604/60 |
| 4,919,664 | 4/1990 | Oliver et al. | 623/15 |
| 4,969,903 | 11/1990 | Valle | 623/15 |

FOREIGN PATENT DOCUMENTS

| | | | |
|---|---|---|---|
| 78 18262 | 3/1979 | France . | |
| 3537514 | 4/1987 | Germany . | |
| 840276 | 7/1960 | United Kingdom | 604/62 |
| 2190845 | 5/1987 | United Kingdom . | |
| 646986 | 2/1979 | U.S.S.R. . | |

Primary Examiner—Stephen C. Pellegrino
Assistant Examiner—Glenn Dawson
Attorney, Agent, or Firm—Merchant, Gould, Smith, Edell, Welter & Schmidt

[57] ABSTRACT

A cosmetic procedure for hair transplantation is carried out with an apparatus (50) comprising a magazine (52) with a plurality of compartments (53) each containing a sample of de-epithelialized tissue having at least one hair shaft attached to a hair bulb. The magazine (52) is loaded in an apparatus (50) having a tapered hollow lumen (57) aligned with a pusher rod (56). With the hollow lumen (57) penetrating a recipient graft site to a predetermined depth and the pusher rod (56), the hollow lumen (57) and a compartment (53) in axial alignment, pusher rod (56) moves through compartment (53) and into the hollow lumen (57) to deposit a portion of donor tissue in the recipient graft site.

6 Claims, 3 Drawing Sheets

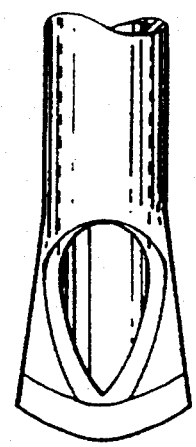
Fig.6A.  Fig.6B.
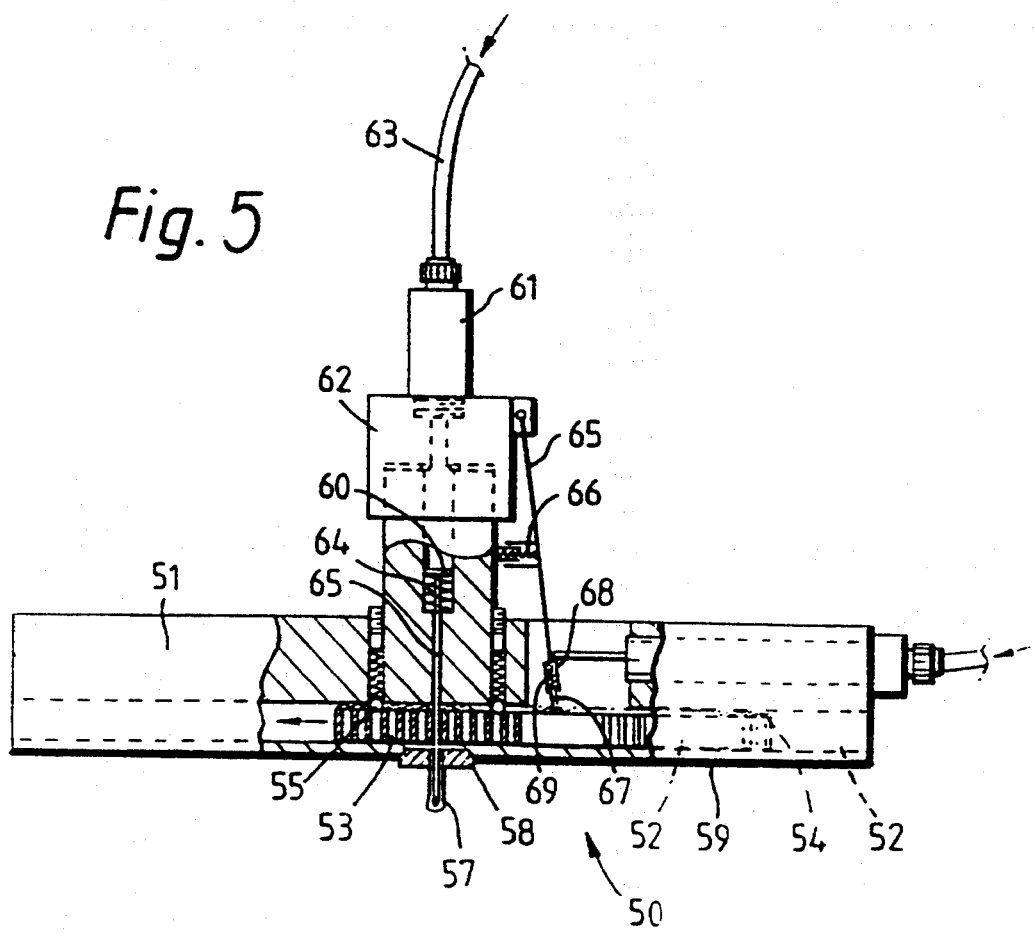
Fig.5

TISSUE GRAFTING METHOD USING AN APPARATUS WITH MULTIPLE TISSUE RECEIVING RECEPTACLES

This invention is concerned with an apparatus and method for transplantation and grafting of specimens of animal issue.

Particularly although not exclusively, this invention is concerned with an apparatus and method of transplantation and grafting of epithelialized and de-epithelialized human tissue containing hair follicles.

There are many techniques available for human "hair transplants" and these techniques vary greatly in effectiveness and cost to the patient.

One prior art technique is known as "punch" grafting wherein a cylindrical plug or other shape of epithelialized tissue is removed from a bald patch of scalp and is replaced by a plug of similar dimensions after (about 4-5 mm in diameter) of tissue containing hair follicles which is removed from another region of the patient's scalp. This technique is slow (and thus costly), painful and usually gives rise to development of unsightly scar tissue. A further disadvantage of this technique is that due to delays in revascularization of the transplanted "plug" there is a higher mortality of hair bulbs in the central region of the relatively large "plugs". Similarly, as the removal of the plug from the donor site is unable to be accurately aligned with hair shafts there is some further loss of otherwise viable hair shafts around the perimeter of the plug due to trauma in cutting the plug shape, if the hair bulb is damaged.

Of more recent times a micrografting technique has found favour. This involves the excision of a section of skin and subcutaneous tissue from a donor site (usually the occipital scalp region) after which the donor site is closed by sutures. The excised portion of tissue is then divided, in a direction parallel to the hair shafts into elongate slivers about 1.5 mm or smaller in diameter. The fatty portion below the epidermis is then removed.

The micrografts so obtained are then inserted into small scalpel incisions with the de-epithelialized micrografts located below the outer surface of the scalp or the epithelialized micrograft lying flush with the scalp surface.

Although generally effective in terms of a successful grafting technique with substantially reduced scarring, "micro-grafting" is extremely slow in terms of preparation and insertion of the individual micrografts and thus necessitates a prolonged period of treatment for a patient. Such prolonged surgical treatments are extremely expensive and generally are available only to patients of substantial means.

Accordingly, it can be seen that the choice of hair transplantation technique for a patient is a compromise between cost, effectiveness and duration of the treatment period.

It is an aim of the present invention to overcome or ameliorate the disadvantages of prior art tissue grafting techniques and to provide a novel apparatus and method to achieve successful and cost effective tissue grafting in patients.

According to one aspect of the invention there is provided an apparatus for tissue transplantation, said apparatus comprising:

storage means adapted to receivably locate in respective receptacles a plurality of prepared portions of tissue;

transfer means adapted to transfer individual portions of said tissue from a respective receptacle to a recipient graft site; and, penetration means associated with said transfer means to penetrate a graft site to a predetermined depth to facilitate deposition of said portion of tissue in a selected region of said graft site.

Suitably said storage means comprises a magazine member having a plurality of spaced storage compartments.

If required said storage compartments may comprise hollow elongate passages in said magazine member, said passages having openings at opposed ends thereof.

Preferably said elongate passages each include a slotted aperture extending longitudinally of a side wall of a respective passage.

The penetration means suitably comprises a thin walled tubular member having a free end sharpened to facilitate penetration of a body of tissue.

Preferably said tubular member is tapered towards its free end.

Most preferably said tubular member comprises a sharpened planar edge at its free end.

Suitably, the penetration means is axially aligned with said transfer means to enable said transfer means to move slidably within a longitudinal aperture therewithin.

Preferably said transfer means comprises an elongate rod member.

The apparatus may comprise register means to axially align a hollow elongate passage of said storage compartment with said transfer means and said penetration means whereby in use said transfer means is adapted to transfer a portion of tissue from said storage compartment to a graft site via said penetration means.

The apparatus may include penetration limiting means to selectively limit the degree of penetration means in a graft site.

The apparatus may also include orientation means to selectively permit penetration of said penetration means into a graft site at a predetermined angle relative to a surface of a graft site.

According to a further aspect of the invention there is provided a method for grafting of animal tissue from a donor site to a graft site, said method comprising the steps of:

removing a sample of tissue from a donor site;

dividing said sample into a plurality of tissue portions of predetermined dimensions; and, injecting said tissue portions into a recipient graft site via a hollow lumen having a sharpened free end.

Preferably said tissue portions are injected to a predetermined depth in said graft site.

If required, said tissue portions may be injected at predetermined spatially separated positions at a graft site.

Suitably, a compressive force is applied to the region of said graft site during injection of tissue portions to prevent ejection of adjacent injected tissue portions.

If required some or all of the tissue portions may include an epithelial layer or alternatively said tissue portions may be de-epithelialized.

If required the tissue portions may be selected to include hair shafts with attached hair bulbs.

The tissue portions may be selected to include sweat glands or other organs associated with subcutaneous tissue.

Preferably said method comprises injection of tissue portions into a graft site by means of an injection apparatus as herein described.

According to yet another aspect of the invention there is provided a hollow lumen for introducing injectable materials into animal tissue, said hollow lumen characterised in that the free end of a generally cylindrical hollow shaft is formed as a planar cutting edge.

In order that the various aspects of the invention may be more clearly understood, reference will now be made to various preferred embodiments illustrated in the accompanying drawings in which:

FIG. 5 shows an alternative embodiment of a transplant apparatus according to the invention.

FIG. 6 shows an injection lumen according to a further aspect of the invention.

Figure 1:
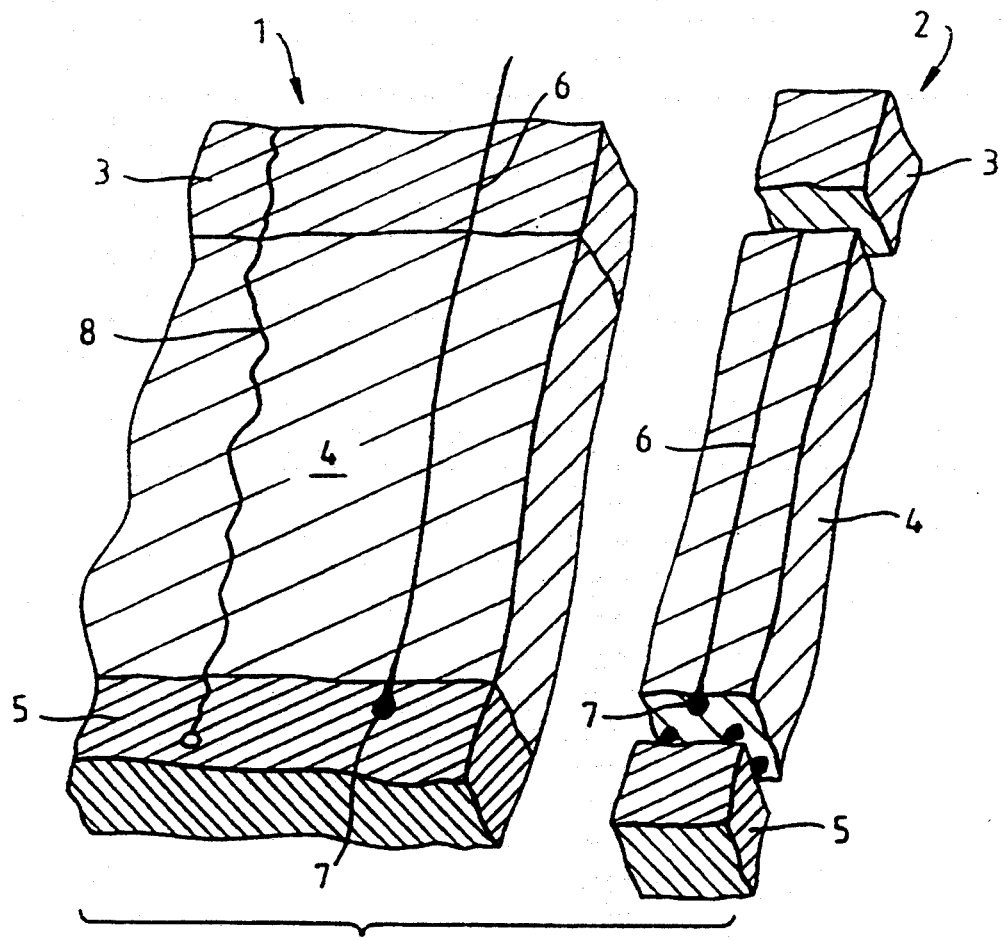
FIG. 1 shows the preparation of a tissue sample for injection grafting.

In FIG. 1 a sample of skin and subcutaneous tissue is taken from a suitable donor site such as the occipital scalp region. The sample is conveniently an ellipse measuring about 80 mm by about 20 mm and the donor site is sutured to close the wound.

The sample is then cut into flat strips about 1.5 mm thick and these strips in turn are cut into portions 2 measuring about 1.5 mm wide. From an elliptical donor site measuring about 80 mm by 20 mm along respective longitudinal axes, about 500 micrografts may be obtained.

Typically the donor sample comprises the epidermis layer 3, the dermis 4 and a layer of fat 5 and may contain from one to three hair follicles. A hair shaft 6 grows from a hair bulb 7 located at the interface of the dermis and fat layers. Other items of interest for grafting purposes may include sweat glands 8. In cutting the portions 2, care is taken to cut parallel to the hair shaft to preserve the integrity of the hair bulb as hair shafts frequently do not grow perpendicularly to the outer surface of the skin.

The sample 2 is then further prepared by excising the epidermis 3 and the fat layer 5 taking care not to damage the hair bulbs 7.

Figure 2:
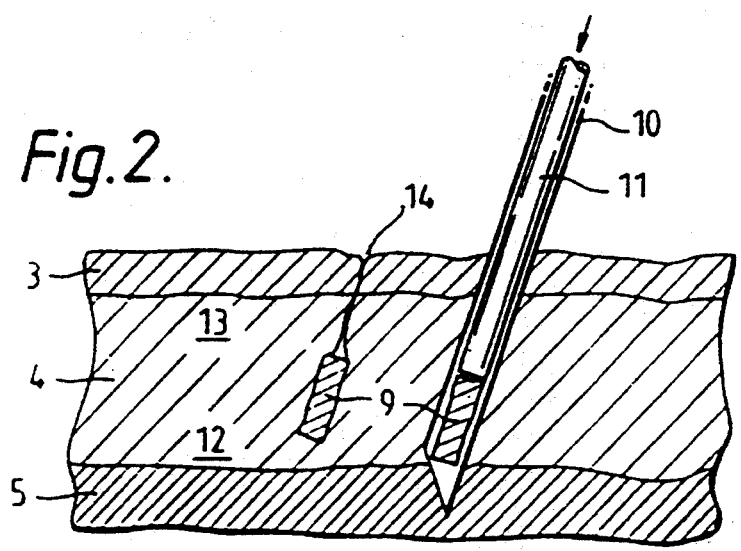
FIG. 2 shows the injection of the tissue sample of FIG. 1 in a graft site.

As shown in FIG. 2 the defatted and de-epithelialized tissue portion 9 may be introduced into the dermis 3 at the graft site by a hollow pointed lumen 10 having a slidable plunger 11 therein.

The dermis 3 has more vascularity and lymphatic activity in the reticular layer 12 than the papillary layer 13 and for this reason it is preferred to utilize de-epithelialized micro grafts as, being smaller than micro grafts with an attached epithelium, they may be completely surrounded by highly vascular tissue, This not only increases the chances of a successful graft but also reduces the amount of surface scar tissue 14.

The technique broadly described above may also be used with micrografts having a retained epithelial layer. Essentially the same technique is employed except that the degree of penetration of the lumen 10 into the graft site may be reduced and/or the stroke of the plunger 11 may be reduced to prevent the epithelial layer of the micrograft being pushed below the epithelial layer of the surrounding graft site.

Figure 3:
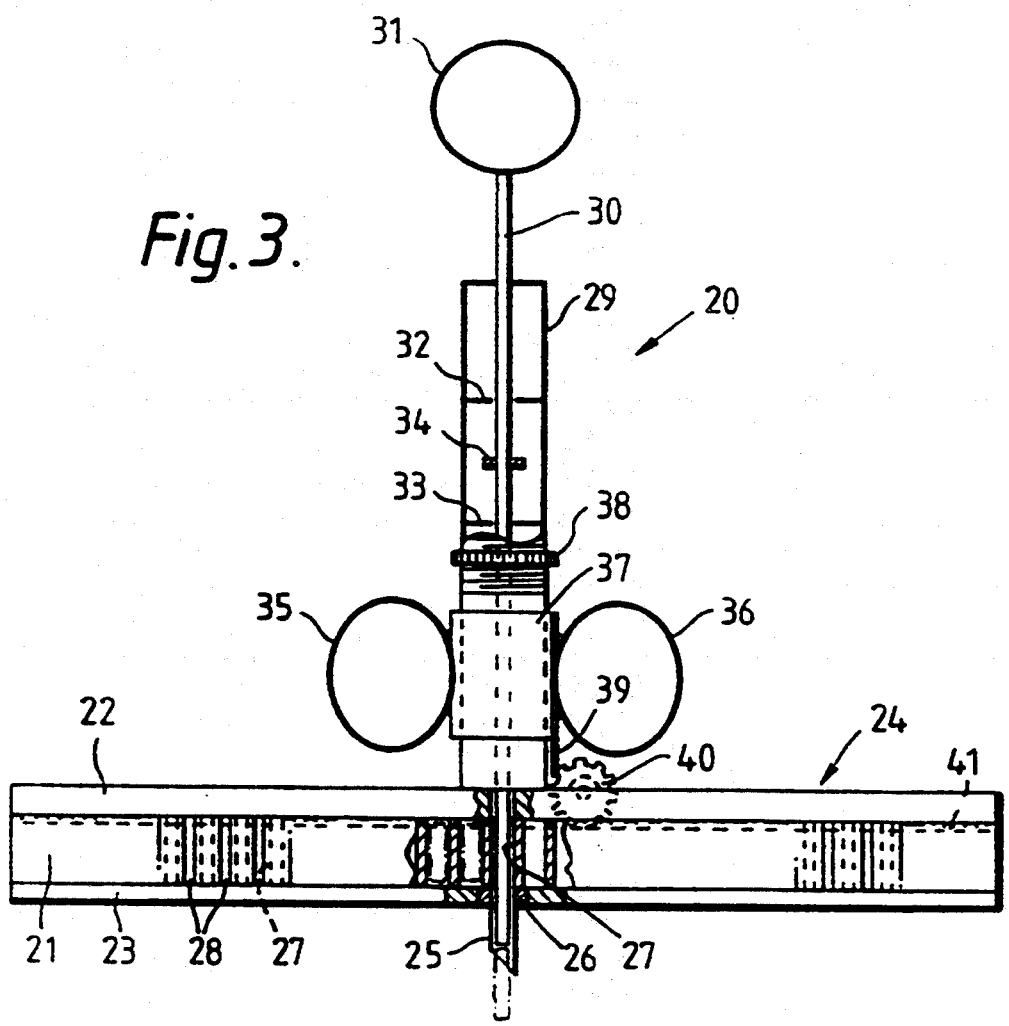
FIG. 3 shows a side elevation of an apparatus according to the invention.

FIG. 3 illustrates schematically an apparatus suitable for carrying out the micro grafting technique described above.

The apparatus 20 comprises a tissue sample magazine 21 slidably located between opposed faces 22,23 of a magazine holder 24. In the lower face 23 of magazine holder 24 is a hollow pointed lumen 25 adapted for removable attachment to magazine holder 24 by a screw threaded flange or the like 26. Magazine 21 includes a plurality of spaced apertures 27 extending between the upper and lower faces of the magazine body. Apertures 27 also comprise slotted opening 28 in a side wall of magazine 21, the purpose of which openings will be described later with reference to FIG. 4.

Mounted on magazine holder 24 is a tubular support member 29 which supports a plunger rod 30 for reciprocating sliding movement. A ring 31 to locate a user's thumb is provided on the upper end of rod 30.

Located within tubular member 29 are abutments 32,33 which cooperate with projection 34 on rod 30 to limit the extent of reciprocation of rod 30. Abutments 32,33 and on projection 34 are adjustable to selectively limit the extent of movement of rod 30.

Ring shaped finger grips 35,36 are provided on a collar 37 slidably mounted on support member 29. An adjustable stop limit 38 is mounted on support member 29 to limit the extent of sliding movement of collar 37.

Mounted on slidable collar 37 is a finger 39 which engages with a toothed wheel 40, the teeth of which engage in a row of teeth 41 formed on magazine 21.

Figure 4:
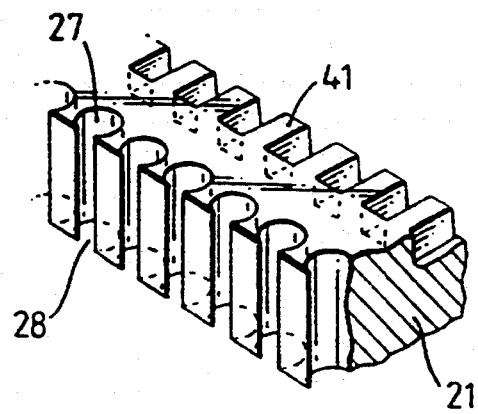
FIG. 4 shows an enlarged partial view of a tissue storage magazine for use with the apparatus of FIG. 3.

FIG. 4 shows an enlarged partial view of magazine 21. Apertures 27 extend between the upper and lower faces of magazine 21 and include an elongate slot 28 on the upright edge of magazine 21. The slot 28 is provided to facilitate loading of micrograft tissue samples into the magazine 21 with minimum handling to avoid unnecessary damage.

After the pre-prepared micrograft portions are loaded into magazine 21, the magazine is itself loaded into the magazine holder of apparatus 20. The magazine is inserted from one end until a first aperture 27 is aligned with plunger rod 30 and lumen 25.

With stops 34 and 38 preset to suit the micrograft procedure and the particular conditions of the recipient graft site and also with a preset length of lumen 25, the micrograft procedure is commenced by inserting lumen 25 into the tissue of the graft site. The lumen is inserted until the lower surface of magazine holder 24 engages the surface of the graft site.

With a thumb inserted in ring 31 and fingers in finger supports 35,36 a squeezing motion is applied between the thumb and fingers whereupon initially, collar 37 moves upwardly until it reaches stop 38. Continued squeezing then causes plunger 30 to move downwardly until it enters an aperture 27 in magazine 21 occupied by a micrograft tissue portion. As the rod passes through aperture 27 it pushes the donor tissue portion through lumen 25 into a desired region in the recipient graft site. The degree of downward movement of rod 30 is limited by the engagement between abutment 33 and projection 34.

Lumen 25 is withdrawn from the recipient graft site and the thumb and fingers are drawn apart to withdraw rod 30 from lumen 25 and aperture 27 in the magazine 21.

As the rod 30 is withdrawn from aperture 27, projection 34 engages abutment 32 and continued finger pressure then causes collar 37 to move downwardly against the influence of a resilient bias such as a spring (not shown) until finger 39 engages toothed wheel 40 causing it to rotate by a predetermined amount to align an adjacent tissue containing aperture 27 with rod 30 and lumen 25. The procedure may then be repeated at an adjacent graft site.

FIG. 5 illustrates an alternative embodiment of the apparatus according to the invention.

The tissue transplant apparatus 50 comprises a body 51 which slidably supports a donor tissue magazine 52. Magazine 52 comprises a plurality of hollow compartments 53 having openings at either end. Donor tissue specimens are pre-loaded into the magazine via longitudinal slots (not shown) in the side wall of each compartment 53 similar to the slots shown in FIG. 4.

Magazines 52 also includes along an upper edge a plurality of ramped teeth 54, the apices of which are at the same intervals as compartments 53. Spring loaded balls 55 are located within body 51 and are adapted to engage in the upper openings of compartments 53 to register the position of respective compartments 53 in axial alignment with pusher rod 56 and replaceable hollow lumen 57.

Located about lumen 57 is a replaceable spacer 58. Spacer 58 comprises an annular washer of silicone rubber or the like and is maintained against the lower face 59 of body 51 by frictional engagement with the outer wall of lumen 57.

Pusher rod 56 is connected to a piston 60 located within cylinder 61 associated with a handle 62 for the apparatus 50. Pusher rod 56 is actuated by a compressed fluid such as air or a pressurized liquid supplied to cylinder 61 via a conduit 63 connected to a foot operated valve (not shown) in turn connected to a source of pressurised fluid. Rod 56 is biassed to a normally retracted position by a spring 64 acting on piston 60.

An arm 65 is pivotted on one end to handle 62 and is biassed to a normally outward position by a spring 66. At the other end of arm 65 is a cylindrical pin 68 slidably located in a housing 68 and is biased outwardly by a spring 69 to engage between the apices of adjacent teeth 54 associated with magazine 52.

The bevelled end of pin 67 enables positive engagement with teeth 54 in one direction to move the magazine 52 in body 51 by squeezing arm 65 against handle 62. The travel of arm 65 is restricted to enable the magazine to advance by a distance equal to the spacing between respective compartments 53. As arm 65 is released spring 66 returns arm 65 to its original position and in so doing, allows bevelled pin 67 to ride up and over the ramped surface of an adjacent tooth by retraction into housing 68 against spring 69.

By providing a foot operated remote actuation for pusher rod 56, the operator of the apparatus has both hands free to accurately position the lumen 57 in a recipient graft site and to operate the apparatus to inject the donor tissue specimens and to advance the magazine 52.

Spacer washer 58 is replaceable with similar washers of differing thickness to permit accurate depth penetration of lumen 57. The spacer washer 57 may be tapered to permit insertion of the donor tissue specimens at angles other than perpendicular to the scalp surface thereby permitting angular protrusion of hair shafts from grafted bulbs to simulate normal adjacent hair growth.

If required, magazine 52 may be selectively-advanced by a further piston and cylinder mechanism powered by pressurised fluid. Similarly, either or both of the pusher rod 56 and the magazine 52 may be actuated by an electro-mechanical means.

In other variations of the invention, the donor tissue magazine may comprise a rotary disk-like member and the hollow lumen 57 may include a knife-like cutting edge as shown in FIG. 6 rather than a conventional tapered point.

FIG. 6 shows a hollow lumen which may be used advantageously with the tissue transplantation apparatus according to invention.

FIG. 6a shows a front elevation of the lumen tip and FIG. 6b shows a side elevation of the tip.

The lumen 70 comprises a hollow cylindrical shaft 71 which makes a shape transition from a circular cross section adjacent the tapered opening 72 to a generally planar blade at its free end 73. The free end 73 is tapered to form a sharpened cutting edge 74.

This type of cutting rather than piercing lumen may be formed by flattening the end of a hollow cylindrical lumen to form a flared shape as shown generally in FIG. 6a with the free end 73 in a planar configuration having the rear wall 75 co-linear with a corresponding portion 76 of the tubular lumen shaft 71.

The front tapering portion of the flattened lumen wall is then ground to form a tapered opening 72 to the cylindrical interior of lumen 70, the tapered opening 72 being surrounded by a side wall 77 with blunt or non sharp edges.

The cutting edge 74 is formed by grinding the free end portion 73 to form a tapered cutting edge 74 as shown.

If required the cutting edge 74 may be formed by tapering both sides of the free end portion 73. Similarly, the cutting edge 74 may be formed as a straight chisel-like cutting edge perpendicular to the longitudinal axis of the lumen or it may be inclined thereto or otherwise shaped to suit.

The "chisel point" lumen 70 according to this aspect of the invention has been found to give a much smoother penetration of scalp tissue with less initial penetration resistance and tissue compression associated with conventional tapered lumen points. Tissue specimens transplated in the miniature incisions formed by these lumen cutting edges not only allow a more precise positioning in the epithelial layer of the recipient graft site but also have demonstrated a greater resistance to dislodgement as a result of pressure adjacent the recipient graft site. Furthermore the extent of scar tissue formation at the recipient graft site been found to be only marginally greater than that which occurs which a conventional tapered lumen point but in any event is substantially undetectable.

It is considered that lumens formed in accordance with this aspect of the invention may have a wide range of applications in surgical and clinical techniques.

For example, when delicate or collapsible tissue is required to be injected with a material, the cutting edge associated with the lumen allows penetration of the tissue without a relatively larger pressure normally associated with conventional tapered lumen. Similarly, insertion of cannulas or the like may be facilitated with a lumen of this type.

In addition the incising lumen according to the invention may be used in microsurgical techniques as a single instrument to effect an initial incision in one or more tissue layers followed by injection of a substance into an underlying layer of tissue.

It will be clear to a skilled addressee that the method and apparatus according to the invention allows the rapid injection of tissue micrografts into a graft site with a minimum amount of scarring and under conditions whereby the success of the graft is maximized.

It will be equally clear to a skilled addressee that while the method and apparatus have been illustrated by reference to a hair transplanting technique, the various aspects of the invention will be applicable to other tissue grafting techniques.

Furthermore, a skilled addressee will readily appreciate that many modifications and variations may be made in the various aspects of the method and apparatus according to the invention without departing from the spirit and scope thereof.

I claim:

1. A method for grafting animal tissue from a donor site to a recipient graft site with an apparatus having storage means comprising a plurality of receptacles, each receptacle being configured to receive a prepared portion of tissue, transfer means adapted to transfer said portions of tissue from said receptacles to said recipient graft site, said transfer means being operatively connected to said receptacles, and hollow penetration means extending along said transfer means for penetrating said recipient graft site to a predetermined depth to facilitate deposition of said prepared portion of tissue in a selected region of said recipient graft site, said method comprising the steps of:

removing a sample of donor tissue from a donor site;

dividing said sample into a plurality of donor tissue portions of predetermined dimensions;

loading said plurality of tissue portions into said receptacles of said storage means;

inserting said hollow penetration means to a predetermined depth in said recipient graft site;

actuating said transfer means to transfer a donor tissue portion from one of said receptacles via said hollow penetration means to said recipient graft site; and withdrawing said hollow penetration means from said recipient graft site to leave said donor tissue portion embedded in said recipient graft site.

2. A method as claimed in claim 1 wherein said donor tissue includes organs associated with subcutaneous tissue.

3. A method as claimed in claim 2 wherein said donor tissue includes hair shafts attached to hair bulbs.

4. A method as claimed in claim 3 wherein said donor tissue includes an epithelial layer.

5. A method as claimed in claim 3 wherein said donor tissue is de-epithelialised.

6. The method of claim 1 wherein said donor tissue includes hair follicles.

* * * * *